(12) United States Patent
Zhou et al.

(10) Patent No.: US 8,802,855 B2
(45) Date of Patent: Aug. 12, 2014

(54) METHOD FOR PREPARATION OF ILOPERIDONE AND CRYSTALLIZATION METHOD THEREOF

(75) Inventors: Shiwei Zhou, Linhai (CN); Feng Jian, Linhai (CN)

(73) Assignee: Zhejiang Huahai Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 13/383,175

(22) PCT Filed: Jun. 21, 2010

(86) PCT No.: PCT/CN2010/074131
§ 371 (c)(1),
(2), (4) Date: Jan. 9, 2012

(87) PCT Pub. No.: WO2011/032404
PCT Pub. Date: Mar. 24, 2011

(65) Prior Publication Data
US 2012/0172600 A1    Jul. 5, 2012

(30) Foreign Application Priority Data

Sep. 19, 2009  (CN) .......................... 2009 1 0178691
Nov. 21, 2009  (CN) .......................... 2009 1 0225973

(51) Int. Cl.
*C07D 413/04* (2006.01)
*A61K 31/445* (2006.01)

(52) U.S. Cl.
USPC ........................................ 546/198; 514/321

(58) Field of Classification Search
USPC ............................................ 514/321; 546/198
See application file for complete search history.

(56) References Cited

U.S. PATENT DOCUMENTS

| 5,185,952 A * | 2/1993 | Bruce ............................. 43/57.1 |
| 5,364,866 A | 11/1994 | Strupczewski et al. |
| 5,776,963 A | 7/1998 | Strupczewski et al. |
| 2005/0250813 A1 | 11/2005 | Wieckhusen et al. |

FOREIGN PATENT DOCUMENTS

| CN | 1048037 A | 12/1990 |
| EP | 0 402 644 A1 | 12/1990 |
| WO | WO2004/006886 * | 1/2004 |

OTHER PUBLICATIONS

Dimethylformamide, Wikipedia p. 1-3 (2013).*
Marks & Spencer p. 1-2 (1991).*
Marzaro et al. "Microwave . . . " Roy. Soc. Chem. supplementary for green chemistry p. 1-5 (2009).*
Solvent, Wikipedia, p. 1-10 (2011).*
International Search Report dated Sep. 16, 2011 from corresponding International Application No. PCT/CN2010/074131.

* cited by examiner

*Primary Examiner* — Celia Chang
(74) *Attorney, Agent, or Firm* — Wolf, Greenfield & Sacks, P.C.

(57) ABSTRACT

A method for preparation of iloperidone is provided which comprises reacting 6-fluoro-3-(4-piperidinyl)-1,2-benzoisoxazole hydrochloride with 1-[4-(3-chloropropoxyl)-3-methoxyphenyl]ethyl ketone in an inorganic alkaline aqueous solution. A crystallization method of iloperidone is also provided which comprises adding seed crystal to the iloperidone solution in ethyl acetate, and then iloperidone crystal is obtained with high purity by controlling the temperature and the stirring speed.

12 Claims, No Drawings

METHOD FOR PREPARATION OF ILOPERIDONE AND CRYSTALLIZATION METHOD THEREOF

The present application claims the priority of the following Chinese patent applications: (1) Chinese patent application No. 200910178691.3 filed to the Chinese Patent Office on Sep. 19, 2009, titled "a new preparation method of iloperidone"; (2) Chinese patent application No. 200910225973.4 filed to the Chinese Patent Office on Nov. 21, 2009, titled "a crystallization method of iloperidone", the entire contents thereof are hereby incorporated by reference.

FIELD OF THE INVENTION

The present invention belongs to the pharmaceutical and chemical field, in particular, relates to a preparation method of an antipsychotic drug iloperidone i.e. 1-(4-(3-(4-(6-fluoro-1,2-benzoisoxazole-3-yl)piperidinyl)propoxyl)-3-methoxyphenyl)ethyl ketone and crystallization method thereof.

BACKGROUND OF THE INVENTION

Iloperidone has a structure represented by formula (I), and its chemical name is 1-(4-(3-(4-(6-fluoro-1,2-benzoisoxazole-3-yl)piperidinyl)propoxyl)-3-methoxyphenyl)ethyl ketone.

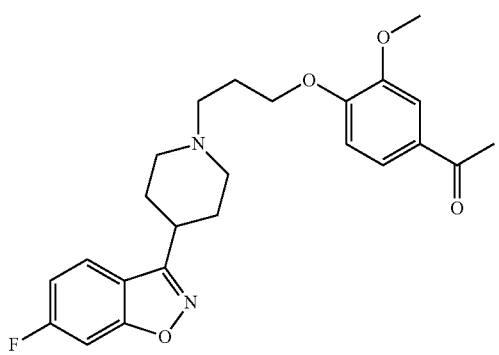

(I)

Iloperidone is a mixed-type dopamine D2/serotonin 5HT2A receptor blocker. Iloperidone has a high affinity for serotonin 5HT2A, and dopamine D2 and D3 receptor, and has a moderate affinity for dopamine D4, and serotonin 5HT6, 5HT7 and norepinephrine NEα1 receptor, and has a low affinity for 5HT1A, dopamine D1 and histamine H1 receptor, and has no detectable affinity for cholinergic muscarine receptors. Iloperidone acts by blocking dopamine D2, D3, serotonin 5HT1A and norepinephrine NEα1/α2c receptor, and it is an atypical antipsychotic.

There are a variety of chemical methods for preparing iloperidone. Preferably, 1-[4-(3-substituted propoxyl)-3-methoxyphenyl]ethyl ketone represented by general formula (II) and 6-Fluoro-3-(4-piperidinyl)-1,2-benzoisoxazole represented by general formula (III) are used to synthesize iloperidone, wherein X is a halogen atom.

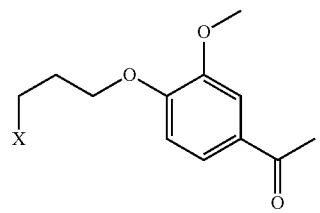

(II)

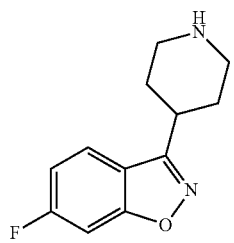

(III)

U.S. Pat. No. 5,776,963 has described a method for synthesis of iloperidone. According to U.S. Pat. No. 5,776,963, iloperidone was obtained by heating 6-fluoro-3-(4-piperidinyl)-1,2-benzoisoxazole hydrochloride and 1-[4-(3-chloropropoxyl)-3-methoxyphenyl]ethyl ketone in dimethylformamide (DMF) in the presence of potassium carbonate to 90° C. and then reaction for 16 hours. This method uses carcinogenic dimethylformamide (DMF) as a solvent, however, potassium carbonate is essentially insoluble in dimethylformamide (DMF), so it is not favorable for 6-fluoro-3-(4-piperidinyl)-1,2-benzoisoxazole to participate the reaction rapidly in free from, moreover, wastes generated by the reaction will result in environmental problems and thus it is necessary to perform special treatments; for the posttreatment, it is necessary to perform extraction using ethyl acetate, and then wash with water, so the posttreatment is complicated. The reaction cycle is as long as 16 hours, and the yield is low (only 58%). Thus, the production cost will be greatly enhanced. Therefore, the iloperidone preparation method described in U.S. Pat. No. 5,776,963 is neither economic nor environment protective.

In addition, U.S. Pat. No. 5,776,963 simply mentioned that the resulting crude iloperidone was recrystallized from ethanol in the synthesis of iloperidone. This method uses ethanol which has a strong polarity as the crystallization solvent, however, the raw materials IV, V and less polar impurities have relatively low solubility in ethanol, as a result, unreacted raw materials IV, V and less polar impurities will co-precipitate with iloperidone which result in decreased crystallization effect, thus, it is necessary to perform purification twice. However, in the crystallization process, crystallization solution is often in a supersaturation state in the absence of seed-induced crystallization, which will lead to a large amount of iloperidone being lost with the crystallization mother liquor. Therefore, use of ethanol as the crystallization solvent will cause a great loss of product, and the yield is not high, so it is not suitable for industrial production.

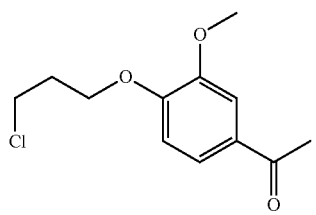

(IV)

-continued

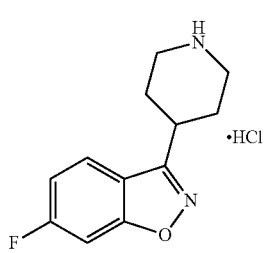

(V)

SUMMARY OF THE INVENTION

The object of the present invention is to provide a more convenient and environmentally friendly preparation method of iloperidone so that the reaction meets the requirements for industrial production in terms of cost and environment. The present invention also provides a crystallization method of iloperidone thereby iloperidone meeting purity requirements can be obtained after crude iloperidone is crystallized once.

In order to achieve this purpose, the present invention provides a method for preparing iloperidone represented by formula (I) comprising reacting 6-fluoro-3-(4-piperidinyl)-1,2-benzoisoxazole hydrochloride represented by formula (V) and 1-[4-(3-chloropropoxyl)-3-methoxyphenyl]ethyl ketone represented by formula (IV) in an inorganic alkaline aqueous solution to obtain crude iloperidone.

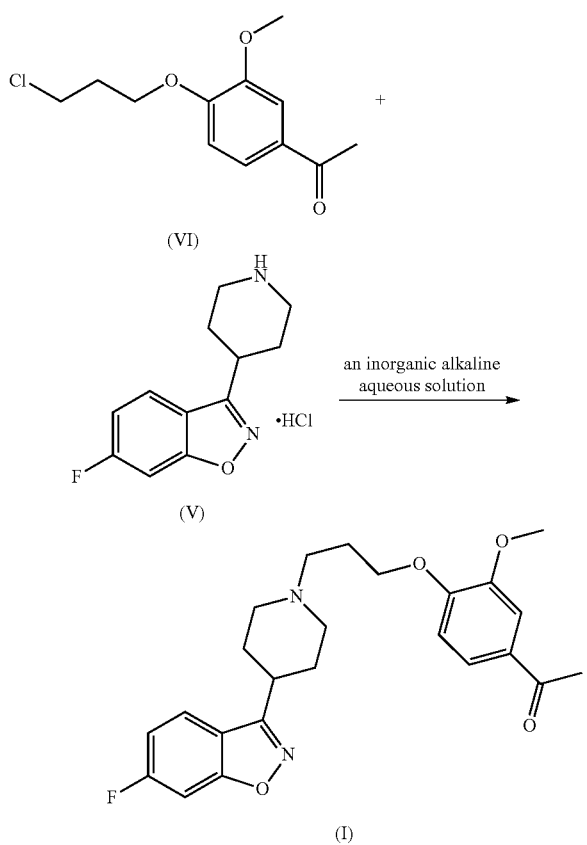

In the preparation method of iloperidone of the present invention, the molar ratio of 6-fluoro-3-(4-piperidinyl)-1,2-benzoisoxazole hydrochloride represented by formula (V) and 1-[4-(3-chloropropoxyl)-3-methoxyphenyl]ethyl ketone represented by formula (IV) is 1:1.0~2.0, preferably 1:1.1~1.3, based on the amount of 6-fluoro-3-(4-piperidinyl)-1,2-benzoisoxazole hydrochloride represented by formula (V).

In the preparation method of iloperidone of the present invention, the inorganic alkaline aqueous solution is an alkali metal carbonate aqueous solution.

In the preparation method of iloperidone of the present invention, the percent by weight of alkali metal carbonate in the inorganic alkaline aqueous solution is 10% to 30%, preferably 13%.

In the preparation method of iloperidone of the present invention, the alkali metal carbonate in the inorganic alkaline aqueous solution is sodium carbonate, potassium carbonate or mixture thereof, preferably potassium carbonate.

In the preparation method of iloperidone of the present invention, the volume of the inorganic alkaline aqueous solution is 5 ml-20 ml, preferably 12 ml-15 ml, relative to 1 g of 6-fluoro-3-(4-piperidinyl)-1,2-benzoisoxazole hydrochloride represented by formula (V).

In the preparation method of iloperidone of the present invention, the reaction temperature is in the range of 60° C.~100° C., preferably 80° C.~90° C., and the reaction time is 0.5 hour to 3 hours, preferably 1.5 hours to 2 hours.

In the present invention, an appropriate amount of ethyl acetate is used as a crystallization solvent to dissolve crude iloperidone with heating. It was found through experiments that crude iloperidone could be easily dissolved in ethyl acetate when being heated, and iloperidone was readily to precipitate from the iloperidone solution after the temperature was cooled down. Therefore, ethyl acetate is a good solvent for the crystallization of iloperidone. When the volume of ethyl acetate used is 4 ml-6 ml relative to 1 g crude iloperidone, the purification and crystallization effect of iloperidone is best.

The purpose of "the iloperidone solution is slowly cooled to 40° C.-60° C." in the present invention is as follows: (1) to make the iloperidone solution reach a supersaturation state and maintain such a state to avoid spontaneous formation of crystal nucleus; and (2) to control the number of crystal nucleus in the iloperidone solution when the crystal seed is added. It was found through experiment study that when the temperature was controlled at 50° C.-55° C., the iloperidone solution could remain this state for some time and did not cause turbidity in initial crystallization, and maintained an appropriate number of crystal nucleus after addition of the crystal seed.

The purpose of "1% to 5% of the crystal seed relative to the weight of crude iloperidone is added" in the present invention is to obtain uniform particle size of product by adding an appropriate number of crystal seed with appropriate size to the crystallization solution to control the crystal quality during the crystallization process. The weight of iloperidone crystal seed is preferably 3% relative to the weight of crude iloperidone.

The purpose of "stirring speed is controlled at 60 r/min-120 r/min, and stirring is performed for 1 hour to 3 hours at a constant temperature" in the present invention is to maintain moderate stirring during the crystallization process, so that the crystal seed is more uniformly suspended in the whole solution and the number of the secondary nucleus is reduced, thus, the crystallized material only grows on the surface of the crystal seed. Preferably, stirring speed is 60 r/min-80 r/min, and the stirring is performed for 2 hours to 2.5 hours at a constant temperature.

The purpose of "the resulting solution is slowly cooled to room temperature under stirring, and then continuously stirred for 3 hours to 7 hours" in the present invention is to increase the supersaturation of the crystallizing solution, and thus facilitate the full growth and precipitation of the crystals. The stirring time is preferably 5 hours to 6 hours.

Finally, the resulting crystalline slurry is filtered, and the resulting crystal is washed with ethyl acetate and dried to obtain iloperidone crystal.

The preparation method of iloperidone of the present invention is performed in an inorganic alkaline aqueous solution and avoid the use of organic solvents, thus the reaction time is greatly shortened and the reaction yield can be up to 90% or more. The crude iloperidone obtained by the method of the present invention can be refined by a simple recrystallization step to get iloperidone which purity is more than 99.0%. The yield of this method is high and the cost is low, moreover, it has no adverse effect on operators and environment, thus is very suitable for industrial production.

The present invention provides a crystallization method of iloperidone thereby iloperidone meeting purity requirements can be obtained after crude iloperidone is crystallized once. The reaction yield is higher, so the method is suitable for industrial production.

DETAILED DESCRIPTION OF THE INVENTION

Now the present invention will be further illustrated in combination with the following examples, so that those skilled in the art can understand the present invention better, however, the scope of the present invention will, not be limited in any way.

In the preparation method provided in the present invention, crude iloperidone is obtained rapidly and efficiently by reacting commercially available raw material 6-fluoro-3-(4-piperidinyl)-1,2-benzoisoxazole hydrochloride represented by formula (V) with commercially available raw material 1-[4-(3-chloropropoxy)-3-methoxyphenyl]ethyl ketone represented by formula (IV) in an inorganic alkaline aqueous solution, and then iloperidone which purity is higher than 99.0% can be obtained by refining. The reaction scheme for preparing crude iloperidone is as follows:

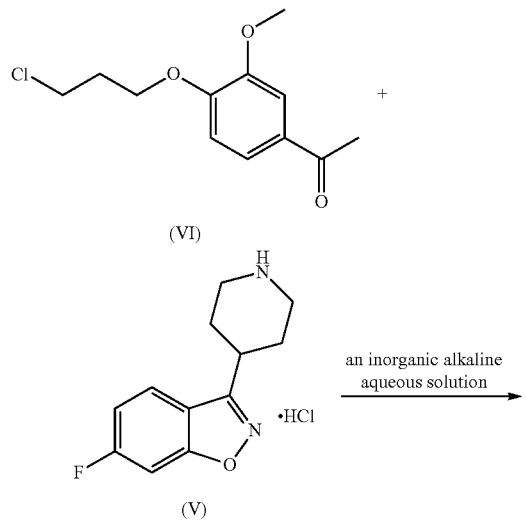

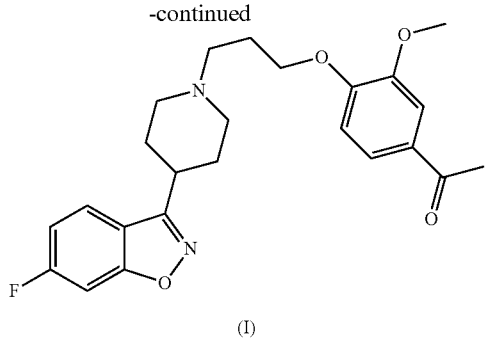

The specific preparation method of iloperidone is as follows:

Example 1

10 g of reactant 6-fluoro-3-(4-piperidinyl)-1,2-benzoisoxazole hydrochloride and 10.4 g of reactant 1-[4-(3-chloropropoxy)-3-methoxyphenyl]ethyl ketone were placed in a 250 ml reaction flask, and a solution prepared with 17.9 g potassium carbonate and 120 ml water was added thereto. The reaction mixture was heated to 80-90° C. and stirred for 1.5 hours, then naturally cooled to room temperature under stirring and filtered. The filter cake was washed twice with water, and then washed twice with methanol, and dried in vacuum at 50° C. to obtain 15.1 g crude iloperidone. The yield was 91.0%. The crude product was decolored by active carbon, then recrystallized with toluene to obtain iloperidone. The purity was 99.5% (determined by HPLC), and the melting point was 118-120° C.

Example 2

10 g of reactant 6-fluoro-3-(4-piperidinyl)-1,2-benzoisoxazole hydrochloride and 13.1 g of reactant 1-[4-(3-chloropropoxy)-3-methoxyphenyl]ethyl ketone were placed in a 250 ml reaction flask, and a solution prepared with 17.9 g sodium carbonate and 140 ml water was added thereto. The reaction mixture was heated to 80-90° C. and stirred 1.5 hours, then naturally cooled to room temperature under stirring and filtered. The filter cake was washed twice with water, and then washed twice with methanol, and dried in vacuum at 50° C. to obtain 14.7 g crude iloperidone. The yield was 88.5%. The crude was decolored by active carbon, and then recrystallized with toluene to obtain iloperidone. The purity was 99.5% (determined by HPLC).

Example 3

10 g of reactant 6-fluoro-3-(4-piperidinyl)-1,2-benzoisoxazole hydrochloride and 14.2 g of reactant 1-[4-(3-chloropropoxy)-3-methoxyphenyl]ethyl ketone were placed in a 250 ml reaction flask, and a solution prepared with 8.9 g sodium carbonate, 9 g potassium carbonate and 150 ml water was added thereto. The reaction mixture was heated to 80-90° C. and stirred 1.5 hours, then naturally cooled to room temperature under stirring and filtered. The filter cake was washed twice with water, and then washed twice with methanol, and dried in vacuum at 50° C. to obtain 14.9 g crude iloperidone. The yield was 89.7%. The crude product was decolored by active carbon, and then recrystallized with toluene to obtain iloperidone. The purity was 99.5% (determined by HPLC).

Example 4

10 g of reactant 6-fluoro-3-(4-piperidinyl)-1,2-benzoisoxazole hydrochloride and 16.4 g of reactant 1-[4-(3-chloropropoxyl)-3-methoxyphenyl]ethyl ketone were placed in a 250 ml reaction flask, and a solution prepared with 30 g potassium carbonate and 60 ml water was added thereto. The reaction mixture was heated to 60-70° C. and stirred for 2.5 hours, then naturally cooled to room temperature under stirring and filtered. The filter cake was washed twice with water, and then washed twice with methanol, and dried in vacuum at 50° C. to obtain 14.3 g crude iloperidone. The yield was 86.1%. The crude product was decolored by active carbon, and then recrystallized with toluene to obtain iloperidone. The purity was 99.5% (determined by HPLC).

Example 5

10 g of reactant 6-fluoro-3-(4-piperidinyl)-1,2-benzoisoxazole hydrochloride and 17.5 g of reactant 1-[4-(3-chloropropoxyl)-3-methoxyphenyl]ethyl ketone were placed in a 250 ml reaction flask, and a solution prepared with 30 g potassium carbonate and 80 ml water was added thereto. The reaction mixture was heated to 90° C.-100° C. and stirred for 1 hour, then naturally cooled to room temperature under stirring and filtered. The filter cake was washed twice with water, and then washed twice with methanol, and dried in vacuum at 50° C. to obtain 15.3 g crude iloperidone. The yield was 92.2%. The crude product was decolored by active carbon, and then recrystallized with toluene to obtain iloperidone. The purity was 99.5% (determined by HPLC).

Example 6

10 g of reactant 6-fluoro-3-(4-piperidinyl)-1,2-benzoisoxazole hydrochloride and 18.6 g of reactant 1-[4-(3-chloropropoxyl)-3-methoxyphenyl]ethyl ketone were placed in a 250 ml reaction flask, and a solution prepared with 17.9 g potassium carbonate and 100 ml water was added thereto. The reaction mixture was heated to 70° C.~80° C. and stirred for 2 hours, then naturally cooled to room temperature under stirring and filtered. The filter cake was washed twice with water, and then washed twice with methanol, and dried in vacuum at 50° C. to obtain 14.9 g crude iloperidone. The yield was 89.8%. The crude product was decolored by active carbon, and then recrystallized with toluene to obtain iloperidone. The purity was 99.5% (determined by HPLC).

Example 7

10 g of reactant 6-fluoro-3-(4-piperidinyl)-1,2-benzoisoxazole hydrochloride and 21.8 g of reactant 1-[4-(3-chloropropoxyl)-3-methoxyphenyl]ethyl ketone were placed in a 250 ml reaction flask, and a solution prepared with 17.9 g sodium carbonate and 180 ml water was added thereto. The reaction mixture was heated to 80° C.~90° C. and stirred for 3 hours, then naturally cooled to room temperature under stirring and filtered. The filter cake was washed twice with water, and then washed twice with methanol, and dried in vacuum at 50° C. to obtain 14.5 g crude iloperidone. The yield was 87.3%. The crude product was decolored by active carbon, and then recrystallized with toluene to obtain iloperidone. The purity was 99.5% (determined by HPLC).

Example 8

10 g of reactant 6-fluoro-3-(4-piperidinyl)-1,2-benzoisoxazole hydrochloride and 10.9 g of reactant 1-[4-(3-chloropropoxyl)-3-methoxyphenyl]ethyl ketone were placed in a 250 ml reaction flask, and a solution prepared with 30 g potassium carbonate and 200 ml water was added thereto. The reaction mixture was heated to 90° C.-100° C. and stirred for 0.5 hour, then naturally cooled to room temperature under stirring and filtered. The filter cake was washed twice with water, and then washed twice with methanol, and dried in vacuum at 50° C. to obtain 14.8 g crude iloperidone. The yield was 89.1%. The crude product was decolored by active carbon, and then recrystallized with toluene to obtain iloperidone. The purity was 99.5% (determined by HPLC).

The present invention also provides a crystallization method of iloperidone comprising using an appropriate amount of ethyl acetate as a solvent for the crystallization of crude iloperidone. The specific crystallization method is as follows:

Example 9

100 g of crude iloperidone prepared in Example 1 and 500 ml ethyl acetate were added to a reaction flask, heated to 80° C. and dissolved by stirring. The insoluble material was filtered while being hot. The resulting iloperidone solution was slowly cooled to 50° C., and 3 g of iloperidone crystal seed was slowly added thereto. The resulting solution was stirred at a speed of 60 r/min, and continuously stirred for 2 hours at this temperature. Next, the solution for crystallization of iloperidone was slowly cooled down to room temperature and continuously stirred for 5 hours. The crystalline slurry was separated by filtration under reduced pressure. The resulting crystals were washed with ethyl acetate, and dried in vacuum to get 78.6 g iloperidone. The yield was 78.6% and the purity was 99.5% (determined by HPLC).

The resulting iloperidone was measured by Japan Rigaku D/max 2550PC automatic multi-crystal X-ray Diffractometer (copper cathode). The interplanar spacing d, Bragg angle $2\theta$, intensity and relative intensity (expressed as a percentage relative to the strongest ray) were as follows:

| $2\theta$ (°) found | D (Å) found | intensity (%) found |
|---|---|---|
| 7.146 | 12.3603 | 3.0 |
| 10.129 | 8.7262 | 1.0 |
| 11.905 | 7.4277 | 1. |
| 12.666 | 6.9834 | 1 |
| 14.332 | 6.1748 | 1.8 |
| 14.852 | 5.9599 | 6.2 |
| 16.776 | 5.2806 | 0.8 |
| 17.154 | 5.1649 | 10.7 |
| 17.548 | 5.0499 | 100.0 |
| 18.264 | 4.8535 | 4.8 |
| 19.409 | 4.5697 | 1.8 |
| 19.967 | 4.4431 | 1.5 |
| 20.357 | 4.3590 | 8.3 |
| 20.716 | 4.2842 | 17.6 |
| 21.565 | 4.1174 | 18.6 |
| 22.151 | 4.0098 | 10.2 |
| 23.266 | 3.8201 | 13.1 |
| 23.606 | 3.7659 | 2.8 |
| 23.959 | 3.7112 | 8.1 |
| 25.159 | 3.5368 | 13.7 |
| 26.333 | 3.3817 | 1.1 |
| 28.963 | 3.0804 | 3.5 |
| 30.508 | 2.9278 | 1.7 |
| 30.752 | 2.9051 | 1.4 |
| 31.815 | 2.8105 | 1.9 |
| | | 8.5 |

Example 10

100 g crude iloperidone prepared in Example 1 and 600 ml ethyl acetate were added to a reaction flask, heated to 70° C. and dissolved under stirring. The insoluble material was filtered while being hot. The resulting iloperidone solution was slowly cooled to 40° C., and 1.5 g iloperidone crystal seed was slowly added thereto. The resulting solution was stirred at a speed of 60 r/min, and continuously stirred for 1 hour at this temperature. Next, the solution for crystallization of iloperidone was slowly cooled to room temperature and continuously stirred for 3 hours. The crystalline slurry was separated by filtration under reduced pressure. The resulting crystals were washed with ethyl acetate, and dried in vacuum to get 76.7 g iloperidone. The yield was 76.7% and the purity was 99.5% (determined by HPLC).

Example 11

100 g crude iloperidone prepared in Example 1 and 400 ml ethyl acetate were added to a reaction flask, heated to 75° C. and dissolved under stirring. The insoluble material was filtered while being hot. The resulting iloperidone solution was slowly cooled to 55° C., and 5 g iloperidone crystal seed was slowly added thereto. The resulting solution was stirred at a speed of 80 r/min, and continuously stirred for 3 hours at this temperature. Next, the solution for crystallization of iloperidone was slowly cooled to room temperature and continuously stirred for 7 hours. The crystalline slurry was separated by filtration under reduced pressure. The resulting crystals were washed with ethyl acetate, and dried in vacuum to get 80.1 g iloperidone. The yield was 80.1% and the purity was 99.5% (determined by HPLC).

Example 12

100 g crude iloperidone prepared in Example 1 and 500 ml ethyl acetate were added to a reaction flask, heated to 80° C. and dissolved under stirring. The insoluble material was filtered while being hot. The resulting iloperidone solution was slowly cooled to 60° C., and 3 g iloperidone seed crystal was slowly added thereto. The resulting solution was stirred at a speed of 70 r/min, and continuously stirred for 1.5 hours at this temperature. Next, the solution for crystallization of iloperidone was slowly cooled to room temperature and continuously stirred for 6 hours. The crystalline slurry was separated by filtration under reduced pressure. The resulting crystals were washed with ethyl acetate, and dried in vacuum to get 77.5 g iloperidone. The yield was 77.5% and the purity was 99.5% (determined by HPLC).

The present invention has described the method for preparing iloperidone and crystallization method thereof in detail. The specific examples in the present invention were used to illustrate the principles and implementation of the present invention. The illustration of the above-mentioned embodiments is merely used to help understanding the method and its core ideas of the present invention. It should be noted that a number of improvements and modifications can also be made on the present invention by those skilled in the art without departing from the principle of the present invention. These improvements and modifications also fall within the protection scope of the claims of the invention.

What is claimed is:

1. A method for preparing iloperidone represented by formula (I) which chemical name is 1-(4-(3-(4-(6-fluoro-1,2-benzoisoxazole-3-yl)piperidinyl)propoxyl)-3-methoxyphenyl)ethyl ketone:

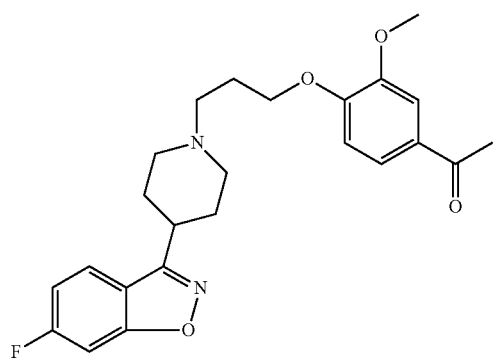

characterized in that it comprises reacting raw material 6-fluoro-3-(4-piperidinyl)-1,2-benzoisoxazole hydrochloride represented by formula (V)

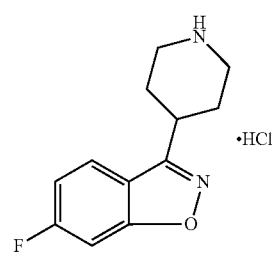

with raw material 1-[4-(3-chloropropoxyl)-3-methoxyphenyl]ethyl ketone represented by formula (IV)

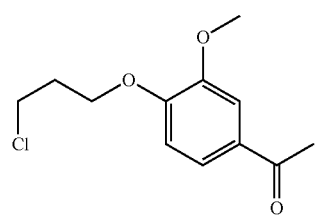

in an inorganic alkaline aqueous solution to prepare iloperidone represented by formula (I).

2. The method for preparing iloperidone according to claim 1, characterized in that the molar ratio of 6-fluoro-3-(4-piperidinyl)-1,2-benzoisoxazole hydrochloride represented by formula (V) and 1-[4-(3-chloropropoxyl)-3-methoxyphenyl] ethyl ketone represented by formula (IV) is 1:1.0~2.0.

3. The method for preparing iloperidone according to claim 1, characterized in that the volume of the inorganic alkaline aqueous solution is 5 ml-20 ml relative to 1 g 6-fluoro-3-(4-piperidinyl)-1,2-benzoisoxazole hydrochloride by formula (V).

4. The method for preparing iloperidone according to claim 1, characterized in that the volume of the inorganic alkaline aqueous solution is 12 ml-15 ml relative to 1 g 6-fluoro-3-(4-piperidinyl)-1,2-benzoisoxazole hydrochloride represented by formula (V).

5. The method for preparing iloperidone according to claim 3, characterized in that the inorganic alkaline aqueous solution is an alkali metal carbonate aqueous solution, wherein the percent by weight of the alkali metal carbonate is 10% to 30%.

6. The method for preparing iloperidone according to claim 5, characterized in that the percent by weight of the alkali metal carbonate is 13%.

7. The method for preparing iloperidone according to claim 6, characterized in that the alkali metal carbonate in the inorganic alkaline aqueous solution is sodium carbonate, potassium carbonate or mixture thereof.

8. The method for preparing iloperidone according to claim 7, characterized in that the alkali metal carbonate in the inorganic alkaline aqueous solution is potassium carbonate.

9. The method for preparing iloperidone according to claim 1, characterized in that the reaction temperature is in the range of 60° C.-100° C.

10. The method for preparing iloperidone according to claim 9, characterized in that the reaction temperature is in the range of 80° C.~90° C.

11. The method for preparing iloperidone according to claim 1, characterized in that the reaction time is 0.5 hour to 3 hours.

12. The method for preparing iloperidone according to claim 11, characterized in that the reaction time is 1.5 hours to 2 hours.

* * * * *